(12) United States Patent
Narula et al.

(10) Patent No.: US 6,617,294 B2
(45) Date of Patent: Sep. 9, 2003

(54) WATERLESS SANITIZING HAND CLEANSER

(76) Inventors: Vinod K. Narula, 9805 Silky Dogwood Ct., Louisville, KY (US) 40241; Dipak Narula, 9428 Wessex Pl., Louisville, KY (US) 40222-5061

( * ) Notice: Subject to any disclaimer, the term of this patent is extended or adjusted under 35 U.S.C. 154(b) by 0 days.

(21) Appl. No.: 10/246,818

(22) Filed: Sep. 18, 2002

(65) Prior Publication Data

US 2003/0139307 A1 Jul. 24, 2003

Related U.S. Application Data

(63) Continuation-in-part of application No. 09/973,327, filed on Oct. 9, 2001, now Pat. No. 6,472,356.
(60) Provisional application No. 60/241,900, filed on Oct. 20, 2000.

(51) Int. Cl.[7] .............................. C11D 3/43; C11D 9/36
(52) U.S. Cl. ...................... 510/138; 510/157; 510/407; 510/432; 510/466
(58) Field of Search ................................ 510/138, 157, 510/407, 432, 466

(56) References Cited

U.S. PATENT DOCUMENTS

| | | | |
|---|---|---|---|
| 5,629,006 A | * | 5/1997 | Hoang et al. ............... 424/405 |
| 5,861,415 A | | 1/1999 | Majeed et al. |
| 5,925,376 A | | 7/1999 | Heng |
| 5,942,478 A | | 8/1999 | Lopes |
| 5,951,993 A | | 9/1999 | Scholz et al. |
| 6,063,381 A | | 5/2000 | Staggs |
| 6,183,766 B1 | * | 2/2001 | Sine et al. ................... 424/405 |
| 6,210,695 B1 | | 4/2001 | Beerse et al. |
| 6,217,887 B1 | | 4/2001 | Beerse et al. |
| 6,238,682 B1 | | 5/2001 | Klofta et al. |
| 6,248,343 B1 | * | 6/2001 | Jampani et al. ............. 424/405 |
| 6,265,363 B1 | * | 7/2001 | Viscovitz .................... 510/130 |
| 6,333,039 B1 | * | 12/2001 | Fendler et al. .............. 424/401 |

* cited by examiner

*Primary Examiner*—Charles Boyer
(74) *Attorney, Agent, or Firm*—Charles G. Lamb; Middleton Reutlinger

(57) ABSTRACT

The present development relates to a liquid cleansing product that effectively reduces the level of microbes on the skin in a relatively short wash time and which dries quickly without causing damage and drying to the skin. The sanitizing cleanser composition comprising an effective amount of alcohol to produce a reduction in microorganisms on the surface of the skin, and an additive to maintain the skin pH in the range of from about 4.0 to about 6.0. The cleanser composition may further include silicone to aid further the drying process, and emollients or oils for skin moisturizing.

60 Claims, No Drawings

WATERLESS SANITIZING HAND CLEANSER

CROSS-REFERENCE TO PRIOR APPLICATIONS

This application claims priority to U.S. patent application Ser. No. 09/973,327, which claims priority from U.S. patent application Ser. No. 60/241,900, filed on Oct. 20, 2000, which is incorporated herein by reference.

BACKGROUND

This invention relates to leave-on, topical antimicrobial compositions that do not require water for antimicrobial effectiveness when applied to the skin. Specifically, the antimicrobial compositions of the present invention use an alcohol based solution to provide an essentially immediate reduction of microorganisms on the skin, a silicone additive to aid in the drying process, and an emollient to leave the skin feeling moisturized.

It is well known that cleansing one's hands with soap and hot water is an effective means of reducing microorganisms on the skin surface. However, if the hands are not thoroughly dried, the trace water residue can harbor bacteria. While this may not pose a serious threat to the population at large, in a hospital setting where the population is more prone to infection, it is desirable to minimize any contamination risks.

In the past few years, research efforts have been directed toward formulating a liquid cleansing product that will effectively sanitize the skin without the use of water. Many of these liquid cleansing products incorporate relatively high concentrations or weight percentages of alcohols in the compositions. The alcohols allow the product to dry quickly, but also cause the skin to dehydrate to an unacceptable degree, irritating the skin and causing it to crack and chafe.

SUMMARY OF THE DEVELOPMENT

The present development relates to a liquid cleansing product that is not water-based. When used topically, the cleansing product effectively reduces the level of microbes on the skin in a relatively short wash time. Further, the cleansing product dries quickly without causing damage and drying to the skin with repeated use. As an added benefit, the cleansing product may provide a moisturizing benefit to the skin.

The present invention provides an antimicrobial sanitizing cleanser composition comprising an effective amount of alcohol to produce a reduction in microorganisms on the surface of the skin and an additive to maintain the skin pH in the range of from about 4.0 to about 6.0. Specifically, an effective amount of lactic acid, fumed silica, sodium lactate or a combination thereof can be added to balance the skin pH. The cleanser composition may further include silicone to aid further the drying process, and emollients or oils for skin moisturizing. The present invention also relates to methods for reducing the level of microorganisms on the skin using the leave-on antimicrobial compositions described herein.

DETAILED DESCRIPTION OF A PREFERRED EMBODIMENT

The present development is a composition for a sanitizing hand cleansing product that is not water based. The product is alcohol based with additives to allow the skin to maintain a pH at from about 4.0 to about 6.0, thus reducing the bacteria count on the skin while maintaining the normal flora of the skin. The composition also includes a silicone component that aids in the drying process, and may also contain emollients which leave the skin feeling moisturized and refreshed. The antimicrobial compositions of the present invention are highly efficacious for reducing the number of microorganisms on the skin while also being moisturizing and protecting to the skin. Further, since the compositions are not water based, several additional advantages are gained over hand cleansing products containing added water. With none to negligible amounts of water present in the compositions of the present invention, the rate of evaporation of the composition from the skin is more consistent than with water present. The humidity of the surrounding air affects the evaporation rate of the water. Thus, a composition containing a significant amount of water would evaporate more slowly from the skin in conditions of higher humidity. Not only does this require the consumer to spend more time rubbing the compound on the skin, it also leaves a tacky or clammy feeling on the skin. The compositions of the present application do not suffer from these detriments since there is no added water in the compositions and the evaporation rates of the alcohol and volatile silicone components are not affected by air humidity.

The sanitizing hand cleanser includes one or more alcohols to provide antimicrobial functionality, to assist in the drying process, and to serve as a solvent. Preferably, the alcohols are approved for use on human skin, such as ethanol, isopropanol, or a combination thereof. The alcohols are present in the formulation at a concentration of from about 60 wt. % to about 90 wt. %.

The hand cleanser also includes one or more additives to allow the skin to maintain a pH of from about 4.0 to about 6.0, such as fumed silica, lactic acid, sodium lactate or a combination thereof. In this pH range, the bacteria count on the skin is reduced while the normal flora of the skin is maintained, potentially providing additional antimicrobial benefits for the cleansing product. An effective amount of additive is included in the formulation to maintain the desired skin pH range, and the amount of additive may range from about 0 wt. % to about 12 wt. %, depending on the additive or combination of additives included in the formulation.

One or more silicone-based materials are included in the hand cleanser formulation to further aid the drying process. The volatile silicones utilized in the compositions of the present invention have a lower heat of evaporation than alcohol, and as such do not create the unpleasant cooling effect on the skin observed with pure alcohol formulations. Further, use of silicone-based materials can lower the surface tension of the fluid composition. This provides greater contact with the skin and therefore more of the fluid can come in contact with detrimental microorganism to provide better overall killing activity. The silicone-based materials, such as cyclomethicone, trimethylsiloxy silicate or a combination thereof, are included in the formulation at a concentration of from about 4 wt. % to about 50 wt. % and more preferably from about 5 wt. % to about 35 wt. %, and even more preferably from about 11 wt. % to about 25 wt. %.

As is known in the art, humectants are added to assist in the retention of liquids within the product, and thickening agents are added to modify the product viscosity. In the present development, any humectant or thickener which does not significantly alter the ability of the formulation to maintain the skin at the desired pH can be used, with the humectant included at a concentration of from about 0 wt. % to about 5 wt. % and the thickener included at a concentration of from about 0 wt. % to about 6.5 wt. %. The thickener may be a cellulose-based material, fumed silica, or a combination thereof, such as methyl cellulose added at concentrations of about 0 wt. % to about 1.5 wt. % used in combination with fumed silica added at concentrations of about 0 wt. % to about 5.0 wt. %.

The hand cleanser may also optionally contain additional antimicrobial agents to enhance the germicidal effects of the alcohol. Exemplary agents include para-chloro-meta-xylenol (PCMX), chlorhexidene gluconate (CHG), triclosan, quaternary ammonium salts like benzalkonium chloride, benzethonium chloride and cetrimide, and other agents as are generally known in the art. These agents may be employed in the composition at a range of between about 0.25 wt. % and about 10 wt. % or at a concentration known to be effective as an antimicrobial. As a representative and non-limiting example, PCMX can be included in the composition of the present invention at a concentration known to provide safe antimicrobial action of from about 2 wt. % to about 3.75 wt. %.

Optionally, emollients and aesthetic additives, such as fragrance and/or colorants may also be added to the sanitizing hand cleanser formulation. Emollients or moisturizing agents, fragrance and colorants are added as necessary and at concentrations for consumer acceptance. For example, the formulation may include from about 0 wt. % to about 1.5 wt. % fragrance, dye or a combination thereof. The formulation may also include from about 0 wt. % to about 5 wt. % of additional emollients, such as, tea tree oil, hemp oil, aloe-based oil, lanolin, jojoba, chamomile, floral oils, herbal materials or a combination thereof are added to the cleansing product to further aid skin moisturization.

The product is prepared by combining the alcohols, the silicone-based materials, the humectants, and the lactic acid or sodium lactate at ambient temperature in a batch mixing vessel and mixing until well blended. Then a portion of the alcohol mixture is removed to a separate mixing vessel and the thickening agents are added, with mixing, until the mixture thickens slightly. Optionally, the fumed silica is then added to the thickening agent mixture to cause the mixture to thicken further. The thickening agent mixture is then combined with the remaining alcohol mixture while maintaining continuous mixing. The resulting product should have a viscosity that allows the product to be dispensed through a hand-pump, such as is commonly used on liquid soap dispensing bottles. For example, the viscosity could range from about 100 centipoise (cp) to about 100,000 cp at about 25° C. The fragrance may be added at any time that allows for good mixing, such as with the alcohol.

The finished product may be incorporated into applicators for specific uses. For example, the product may be added to the sponge of a surgical scrub brush. The brush with incorporated hand scrub can then be used by surgical personnel as part of their aseptic prepping prior to surgery. Alternatively, the product can be incorporated into a woven or non-woven wipe. The wipes can be packaged either individually or together. The wipes with sanitizing cleanser make for a convenient product for cleansing a practitioner's hands or a local portion of a patient before or after examination.

The following examples are representative of the hand cleansers which can be prepared in accordance with the present invention. The antimicrobial performance data of some of the cleansers are also included. The cleanser formulations presented are intended for example purposes only and are not intended to be limiting in scope.

EXAMPLE 1

A sanitizing hand cleanser is prepared which includes about 70 wt. % anhydrous ethanol (3% isopropyl alcohol), about 18.6 wt. % Dow Corning® 345 Fluid (cyclomethicone), about 4.5 wt. % isopropyl myristate, about 1.5 wt. % lactic acid, about 1.5 wt. % sodium lactate (40% active), about 1.3 wt. % Dow Corning® 749 (cyclomethicone and trimethylsiloxysilicate product), about 0.6 wt. % Dow Methocel® OS (methylated cellulose), and about 2.0 wt. % Cabosil M5 fumed silica, commercially available from Cabot Corporation. The product is prepared by mixing the anhydrous ethanol, the 345 Fluid, the isopropyl myristate, the lactic acid, the sodium lactate, and the Dow Corning 749 at ambient temperature in a batch mix tank fitted with at least one agitator or mixing blade until the alcohol mixture is well mixed. Then about 30% of the alcohol mixture is removed to a separate mixing vessel fitted with mixing blades and the Methocel® is added, with mixing, until the mixture thickens slightly. The fumed silica is then added to the Methocel® mixture to cause the mixture to thicken further. The fumed silica/Methocel® mixture is then combined with the remaining alcohol mixture, with continuous mixing, until the fumed silica mixture is completely dissolved in the alcohol mixture. The resulting product has a pH of about 4.5 and has a viscosity of about 350 cp at about 25° C.

EXAMPLE 2

A sanitizing hand cleanser is prepared which includes about 77.6 wt. % anhydrous ethanol (3% isopropyl alcohol), about 15.5 wt. % Dow Corning® 345 Fluid (cyclomethicone), about 1.5 wt. % isopropyl myristate, about 3.6 wt. % sodium lactate (40% active), about 1.0 wt. % Dow Corning® 749 (cyclomethicone and trimethylsiloxysilicate product), about 0.5 wt. % Dow Methocel® OS, and about 0.3 wt. % fragrance. The product is prepared by mixing the anhydrous ethanol, the 345 Fluid, the isopropyl myristate, the sodium lactate, the Dow Corning 749 and the fragrance at ambient temperature in a batch mix tank fitted with at least one agitator or mixing blade until the alcohol mixture is well mixed. Then about 30% of the alcohol mixture is removed to a separate mixing vessel fitted with mixing blades and the Methocel® is added, with mixing, until the mixture thickens slightly. The Methocel® mixture is then combined with the remaining alcohol mixture, with continuous mixing, until the Methocel® mixture is completely dissolved in the alcohol mixture. The resulting product has a pH of about 4.3 and has a viscosity of about 340 cp at about 25° C.

EXAMPLE 3

A sanitizing hand cleanser is prepared which is identical to the product of Example 2 except that about 1.5 wt. % of tea tree oil is substituted for about 1.5 wt. % anhydrous ethanol (3% isopropyl alcohol). The product is prepared as in Example 2 with the tea tree oil added in the alcohol mixture. The resulting product has a pH of about 4.4 and has a viscosity of about 360 cp at about 25° C.

EXAMPLE 4

A sanitizing hand cleanser is prepared which is identical to the product of Example 2 except that about 1.8 wt. % of hemp oil is substituted for about 1.8 wt. % anhydrous ethanol (3% isopropyl alcohol). The product is prepared as in Example 2 with the hemp oil added in the alcohol mixture.

The resulting product has a pH of about 4.3 and has a viscosity of about 350 cp at about 25° C.

EXAMPLE 5

A sanitizing hand cleanser is prepared which is identical to the product of Example 2 except that about 1.0 wt. % of tea tree oil and about 0.5 wt. % of hemp oil is substituted for about 1.5 wt. % anhydrous ethanol (3% isopropyl alcohol). The product is prepared as in Example 2 with the tea tree oil and hemp oil added in the alcohol mixture. The resulting product has a pH of about 4.3 and has a viscosity of about 365 cp at about 25° C.

Additional Examples

A number of additional hand sanitizing cleanser formulations are prepared generally according to the procedures described above and shown in Table 1. The make up and observations related to the aesthetic quality of the formulations are given in tabular form following. Units are in wt % of total. It is of interest to note that formulations E29, E31, E32 and E33 produced a product that separated. This is likely due to an alcohol concentration that was too low, around 40%, which is below the claimed concentration of the present invention.

TABLE 1

|  | E0 | E1 | E2 | E3 | E4 | E5 | E6 | E7 |
|---|---|---|---|---|---|---|---|---|
| Ethanol, SD3A | 77.6 | 74.70 | 75.30 | 76.82 | 75.00 | 75.00 | 76.82 | 77.4 |
| Isopropyl alcohol | — | — | — | — | 7.10 | 6.10 | — | — |
| Propanol | — | — | — | — | — | — | — | — |
| Butanol | — | — | — | — | — | — | — | — |
| Phenylethyl alcohol | — | — | — | — | — | — | — | — |
| Benzyl Alcohol | — | — | — | — | — | — | — | — |
| PCMX (99%) | — | 3.75 | 3.00 | 1.00 | — | — | — | — |
| CHG (20% in water) | — | — | — | — | — | — | — | — |
| Triclosan (100%) | — | — | — | — | — | — | 1.00 | — |
| QAC- | | | | | | | | |
| Benzalkonium chloride (50% in Water) | — | — | — | — | — | — | — | 0.26 |
| Benzethonium chloride (100%) | — | — | — | — | — | — | — | — |
| Cetramide | — | — | — | — | — | — | — | — |
| DC 345 Fluid | 15.5 | 14.92 | 15.02 | 15.35 | 11.00 | 12.00 | 15.35 | 15.46 |
| DC 200 fluid, 0.65 cst | — | — | — | — | — | — | — | — |
| Propylene Glycol | — | — | — | — | — | — | — | — |
| Glycerin | — | — | — | — | — | — | — | — |
| Sodium Lactate | 3.6 | 3.46 | 3.49 | 3.57 | 3.60 | 3.60 | 3.57 | 3.59 |
| Isopropyl Myristate | 1.5 | 1.44 | 1.45 | 1.49 | 1.50 | 1.50 | 1.49 | 1.50 |
| DC 749 | 1.0 | 0.96 | 0.97 | 0.99 | 1.00 | 1.00 | 0.99 | 1.00 |
| Aloe Vera Extract | — | — | — | — | — | — | — | — |
| Methocel OS | 0.5 | 0.48 | 0.48 | 0.49 | 0.50 | 0.50 | 0.49 | 0.50 |
| Fragrance | 0.3 | 0.29 | 0.29 | 0.29 | 0.30 | 0.30 | 0.29 | 0.29 |
| Observations | 100.00 clear sol. | 100.00 clear sol. | 100.00 clear sol. | 100.00 clear sol. | 100.00 clear sol. | 100.00 clear sol. | 100.00 clear sol. | 100.00 clear sol. |

|  | E8 | E9 | E10 | E11 | E12 | E13 |
|---|---|---|---|---|---|---|
| Ethanol, SD3A | 77.4 | 75.30 | 75.00 | 75.00 | 75.00 | 75.00 |
| Isopropyl alcohol | — | — | — | — | — | — |
| Propanol | — | — | — | 5.00 | — | — |
| Butanol | — | — | — | — | 5.00 | — |
| Phenylethyl alcohol | — | — | — | — | — | 5.00 |
| Benzyl Alcohol | — | — | — | — | — | — |
| PCMX (99%) | — | — | 3.00 | — | — | — |
| CHG (20% in water) | — | — | — | — | — | — |
| Triclosan (100%) | — | — | — | — | — | — |
| QAC- | | | | | | |
| Benzalkonium chloride (50% in Water) | — | — | 0.30 | — | — | — |
| Benzethonium chloride (100%) | 0.26 | — | — | — | — | — |
| Cetramide | — | 3.00 | — | — | — | — |
| DC 345 Fluid | 15.46 | 15.02 | 15.02 | 13.10 | 13.10 | 13.10 |
| DC 200 fluid, 0.65 cst | — | — | — | — | — | — |
| Propylene Glycol | — | — | — | — | — | — |
| Glycerin | — | — | — | — | — | — |
| Sodium Lactate | 3.59 | 3.49 | 3.49 | 3.60 | 3.60 | 3.60 |
| Isopropyl Myristate | 1.50 | 1.45 | 1.45 | 1.50 | 1.50 | 1.50 |
| DC 749 | 1.00 | 0.97 | 0.97 | 1.00 | 1.00 | 1.00 |
| Aloe Vera Extract | — | — | — | — | — | — |
| Methocel OS | 0.50 | 0.48 | 0.48 | 0.50 | 0.50 | 0.50 |
| Fragrance | 0.29 | 0.29 | 0.29 | 0.3 | 0.3 | 0.3 |
| Observations | 100.00 clear sol. | 100.00 clear sol. | 100.00 clear sol. | 100.00 clear sol. | 100.00 clear sol. | 100.00 clear sol. |

TABLE 1-continued

|  | E14 | E15 | E16 | E17 | E18 | E19 | E20 | E21 |
|---|---|---|---|---|---|---|---|---|
| Ethanol, SD3A | 75.00 | 75.00 | 75.00 | 75.00 | 75.00 | 75.00 | 75.00 | 75.00 |
| Isopropyl alcohol | — | — | — | — | 8.10 | — | — | — |
| Propanol | — | — | — | — | — | — | — | — |
| Butanol | — | — | — | — | — | — | — | — |
| Phenylethyl alcohol | — | 2.50 | 2.50 | — | — | — | — | — |
| Benzyl Alcohol | 5.00 | 2.50 | — | — | — | — | — | 3.50 |
| PCMX (99%) | — | — | 2.50 | — | — | — | — | 2.50 |
| CHG (20% in water) | — | — | — | — | — | — | — | — |
| Triclosan (100%) | — | — | — | — | — | — | — | — |
| QAC- | | | | | | | | |
| Benzalkonium chloride (50% in Water) | — | — | — | — | — | — | — | — |
| Benzethonium chloride (100%) | — | — | — | — | — | — | — | — |
| Cetramide | — | — | — | — | — | — | — | — |
| DC 345 Fluid | 13.10 | 13.10 | 13.10 | 13.10 | 10.00 | 8.10 | 8.10 | 8.10 |
| DC 200 fluid, 0.65 cst | — | — | — | — | — | 10.00 | 5.50 | — |
| Propylene Glycol | — | — | — | 5.00 | — | — | 5.50 | 5.00 |
| Glycerin | — | — | — | — | — | — | — | — |
| Sodium Lactate | 3.60 | 3.60 | 3.60 | 3.60 | 3.60 | 3.60 | 3.60 | 3.60 |
| Isopropyl Myristate | 1.50 | 1.50 | 1.50 | 1.50 | 1.50 | 1.50 | 1.50 | 1.50 |
| DC 749 | 1.00 | 1.00 | 1.00 | — | 1.00 | 1.00 | — | — |
| Aloe Vera Extract | — | — | — | 1.00 | — | — | — | — |
| Methocel OS | 0.50 | 0.50 | 0.50 | 0.50 | 0.50 | 0.50 | 0.50 | 0.50 |
| Fragrance | 0.3 | 0.30 | 0.30 | 0.30 | 0.30 | 0.30 | 0.30 | 0.30 |
| Observations | 100.00 clear sol. | 100.00 clear sol. | 100.00 clear sol. | 100.00 clear sol. | 100.00 clear sol. | 100.00 clear sol. | 100.00 clear sol. | 100.00 clear sol. |

|  | E22 | E23 | E24 | E25 | E26 | E27 | E28 |
|---|---|---|---|---|---|---|---|
| Ethanol, SD3A | 75.00 | 85.00 | 80.00 | 85.00 | 85.00 | 60.00 | 46.55 |
| Isopropyl alcohol | — | — | 5.00 | — | — | — | — |
| Propanol | — | — | — | — | — | — | — |
| Butanol | — | — | — | — | — | — | — |
| Phenylethyl alcohol | — | — | — | — | 1.75 | — | — |
| Benzyl Alcohol | 3.50 | — | — | — | — | — | — |
| PCMX (99%) | 2.50 | — | — | — | 2.90 | — | — |
| CHG (20% in water) | — | — | — | — | — | — | — |
| Triclosan (100%) | — | — | — | — | — | — | — |
| QAC- | | | | | | | |
| Benzalkonium chloride (50% in | — | — | — | — | 0.35 | — | — |
| Benzethonium chloride (100%) | — | — | — | — | — | — | — |
| Cetramide | — | — | — | — | — | — | — |
| DC 345 Fluid | 8.10 | 8.10 | 8.10 | 4.10 | 4.10 | 33.10 | 46.55 |
| DC 200 fluid, 0.65 cst | 2.50 | — | — | — | — | — | — |
| Propylene Glycol | 2.50 | — | — | 5.00 | — | — | — |
| Glycerin | — | — | — | — | — | — | — |
| Sodium Lactate | 3.60 | 3.60 | 3.60 | 3.60 | 3.60 | 3.60 | 3.60 |
| Isopropyl Myristate | 1.50 | 1.50 | 1.50 | 1.50 | 1.50 | 1.50 | 1.50 |
| DC 749 | — | 1.00 | 1.00 | — | 0.00 | 1.00 | 1.00 |
| Aloe Vera Extract | — | — | — | — | — | — | — |
| Methocel OS | 0.50 | 0.50 | 0.50 | 0.50 | 0.50 | 0.50 | 0.50 |
| Fragrance | 0.30 | 0.30 | 0.30 | 0.30 | 0.30 | 0.30 | 0.30 |
| Observations | 100.00 clear sol. | 100.00 clear sol. | 100.00 clear sol. | 100.00 clear sol. | 100.00 clear sol. | 100.00 clear sol. | 100.00 clear sol. |

|  | E29 | E30 | E31 | E32 | E33 | E34 | E35 | E36 |
|---|---|---|---|---|---|---|---|---|
| Ethanol, SD3A | 30.00 | 40.00 | 31.00 | 31.00 | 31.00 | 20.00 | 35.00 | 35.00 |
| Isopropyl alcohol | — | — | — | — | — | 20.00 | — | — |
| Propanol | — | — | — | — | — | — | — | — |
| Butanol | — | — | — | — | — | — | — | — |
| Phenylethyl alcohol | — | — | — | — | — | — | — | 5.00 |
| Benzyl Alcohol | — | — | — | — | — | — | 5.00 | — |
| PCMX (99%) | — | — | — | — | — | — | — | — |
| CHG (20% in water) | — | — | — | — | — | — | — | — |
| Triclosan (100%) | — | — | — | — | — | — | — | — |
| QAC- | | | | | | | | |
| Benzalkonium chloride (50% in Water) | — | — | — | — | — | — | — | — |
| Benzethonium chloride (100%) | — | — | — | — | — | — | — | — |
| Cetramide | — | — | — | — | — | — | — | — |

TABLE 1-continued

|  |  |  |  |  |  |  |  |  |
|---|---|---|---|---|---|---|---|---|
| DC 345 Fluid | 63.10 | 53.10 | 31.00 | 31.00 | 46.50 | 53.00 | 53.00 | 26.50 |
| DC 200 fluid, 0.65 cst | — | — | — | — | — | — | — | 26.50 |
| Propylene Glycol | — | — | 31.00 | 15.50 | 15.50 | — | — | — |
| Glycerin | — | — | — | 15.50 | — | — | — | — |
| Sodium Lactate | 3.60 | 3.60 | 3.60 | 3.60 | 3.60 | 3.60 | 3.60 | 3.60 |
| Isopropyl Myristate | 1.50 | 1.50 | 1.60 | 1.60 | 1.60 | 1.60 | 1.60 | 1.60 |
| DC 749 | 1.00 | 1.00 | — | — | — | 1.00 | 1.00 | 1.00 |
| Aloe Vera Extract | — | — | 1.00 | 1.00 | 1.00 | — | — | — |
| Methocel OS | 0.50 | 0.50 | 0.50 | 0.50 | 0.50 | 0.50 | 0.50 | 0.50 |
| Fragrance | 0.30 | 0.30 | 0.30 | 0.30 | 0.30 | 0.30 | 0.30 | 0.30 |
|  | 100.00 | 100.00 | 100.00 | 100.00 | 100.00 | 100.00 | 100.00 | 100.00 |
| Observations | Seperation | clear sol. | Seperation | Seperation | Seperation | clear sol. | clear sol. | clear sol. |

|  | E37 | E38 | E39 | E40 | E41 | E42 |
|---|---|---|---|---|---|---|
| Ethanol, SD3A | 46.50 | 54.50 | 54.00 | 75.00 | 75.00 | 75.00 |
| Isopropyl alcohol | — | — | — | — | — | — |
| Propanol | — | — | — | — | — | — |
| Butanol | — | — | — | — | — | — |
| Phenylethyl alcohol | 6.00 | — | — | — | — | 5.00 |
| Benzyl Alcohol | — | — | — | — | — | — |
| PCMX (99%) | 3.75 | — | 3.00 | — | — | 3.75 |
| CHG (20% in water) | — | — | — | — | — | — |
| Triclosan (100%) | — | — | — | — | — | — |
| QAC- |  |  |  |  |  |  |
| Benzalkonium chloride (50% in | — | — | 0.75 | — | — | — |
| Benzethonium chloride (100%) | — | — | — | — | — | — |
| Cetramide | — | 3.00 | — | — | — | — |
| DC 345 Fluid | 35.00 | 31.00 | 31.00 | 8.10 | 8.10 | 16.25 |
| DC 200 fluid, 0.65 cst | — | — | — | — | — | — |
| Propylene Glycol | 2.50 | 5.00 | 5.00 | 10.00 | 5.00 | — |
| Glycerin | — | — | — | — | 5.00 | — |
| Sodium Lactate | 3.20 | 3.60 | 3.20 | 3.60 | 3.60 | — |
| Isopropyl Myristate | 1.25 | 1.60 | 1.25 | 1.50 | 1.50 | — |
| DC 749 | — | — | — | — | — | — |
| Aloe Vera Extract | 1.00 | 1.00 | 1.00 | 1.00 | 1.00 | — |
| Methocel OS | 0.50 | 0.00 | 0.50 | 0.50 | 0.50 | — |
| Fragrance | 0.30 | 0.30 | 0.30 | 0.30 | 0.30 | — |
|  | 100.00 | 100.00 | 100.00 | 100.00 | 100.00 | 100.00 |
| Observations | clear sol. | clear sol. | clear sol. | clear sol. | clear sol. |  |

Antimicrobial Performance Studies

Antibacterial efficacy of the hand sanitizing cleansers can be evaluated by a variety of known procedures. For example, a minimum inhibitory concentration study may be used to determine the lowest concentration of the cleanser that inhibits growth of a microorganism or a rapid germicidal study may be used to measure the ability of the cleanser to rapidly reduce a known population of microorganisms. Such studies can be conducted using commonly available bacteria and fungi as are listed in Table 2.

TABLE 2

| Organism | ATCC | Organism | ATCC |
|---|---|---|---|
| Aspergillus niger | 6275 | Bacillus cereus | 11778 |
| Streptococcus pneumoniae | 6303 | Staphylococcus epidermidis | 12228 |
| Staphylococcus aureus | 6538 | Listeria monocytogenes | 15313 |
| Salmonella typhi | 6539 | Haemophilus influenzae | 19418 |
| Proteus mirabilis | 7002 | Candida parapsilosis | 22019 |
| Pseudomonas aeruginosa | 9027 | Campylobacter jejuni | 33560 |
| Candida albicans | 10231 | Staphylococcus aureus (MRSA) | 33592 |
| Escherichia coli | 11229 | Escherichia coli 0157:H7 | 43895 |
| Klebsiella pneumonia (sub. species ozaenae) | 11296 | Enterococcus faecium (VRE) | 51559 |

Minimum Inhibitory Concentration Study

The minimum inhibitory concentration (MIC) is the lowest concentration of an antimicrobial agent that inhibits growth of a microorganism. Serial dilutions of the antimicrobial test material are made in broth or agar and then a standardized concentration of the organism is plated onto the agar containing the diluted test material. A variety of organisms are tested against the article to determine the greatest dilution of the article possible while still maintaining antimicrobial efficacy. Specifically, the product of Example 2 ("Product 2") is tested for minimum inhibitory concentration (MIC) following a procedure wherein a 1:2 dilution of a test material, by weight, is prepared in Mueller-Hinton Broth or a Brain Heart Infusion Broth. A 200 μL aliquot of the dilution is added to the first well in a row of a microtiter plate. Dilutions of the product are then made starting from the first well with the wells containing dilutions of 1:2, 1:4, 1:8, 1:10, 1:20, 1:50, 1:80, 1:100, 1:150 and 1:200 of the test material. Bacterial and media control wells are also included.

The bacterial organism of interest is scraped from a culture plate and resuspended in phosphate buffered saline solution to an approximate density of $1.0 \times 10^5$ cells. An inoculum of approximately $5 \times 10^4$ CFU (colony forming units) of each test organism is added to the test wells in a row of the plate and mixed. The plate is incubated at a temperature of $37 \pm 2°$ C. for about 23 hours. Table 3 summarizes the microbial growth in the test wells in terms of showing growth (+) or showing no growth (0). The MIC is considered to be the lowest dilution in which bacterial growth is completely inhibited in duplicate trials.

TABLE 3

| Organism | | Test Material Well Dilutions | | | | | | | | | | Controls | |
| --- | --- | --- | --- | --- | --- | --- | --- | --- | --- | --- | --- | --- | --- |
| ATCC | Rep. | 1:2 | 1:4 | 1:8 | 1:10 | 1:20 | 1:50 | 1:80 | 1:100 | 1:150 | 1:200 | Bacterial | Media |
| 6303 | 1 | 0 | 0 | + | + | + | + | + | + | + | + | + | 0 |
| 6303 | 2 | 0 | 0 | + | + | + | + | + | + | + | + | + | 0 |
| 6538 | 1 | 0 | 0 | + | + | + | + | + | + | + | + | + | 0 |
| 6538 | 2 | 0 | 0 | + | + | + | + | + | + | + | + | + | 0 |
| 6539 | 1 | 0 | 0 | 0 | + | + | + | + | + | + | + | + | 0 |
| 6539 | 2 | 0 | 0 | 0 | + | + | + | + | + | + | + | + | 0 |
| 7002 | 1 | 0 | 0 | + | 0 | + | + | + | + | + | + | + | 0 |
| 7002 | 2 | 0 | 0 | 0 | + | + | + | + | + | + | + | + | 0 |
| 9027 | 1 | 0 | 0 | 0 | + | + | + | + | + | + | + | + | 0 |
| 9027 | 2 | 0 | 0 | 0 | 0 | + | + | + | + | + | + | + | 0 |
| 10231[a] | 1 | 0 | 0 | + | + | + | + | + | + | + | + | + | 0 |
| 10231[a] | 2 | 0 | + | + | + | + | + | + | + | + | + | + | 0 |
| 11229 | 1 | 0 | 0 | + | + | + | + | + | + | + | + | + | 0 |
| 11229 | 2 | 0 | 0 | + | + | + | + | + | + | + | + | + | 0 |
| 11296 | 1 | 0 | 0 | 0 | 0 | + | + | + | + | + | + | + | 0 |
| 11296 | 2 | 0 | 0 | 0 | 0 | + | + | + | + | + | + | + | 0 |
| 11778[b] | 1 | 0 | 0 | 0 | + | + | + | + | + | + | + | + | 0 |
| 11778[b] | 2 | 0 | 0 | 0 | + | + | + | + | + | + | + | + | 0 |
| 12228 | 1 | 0 | 0 | + | + | + | + | + | + | + | + | + | 0 |
| 12228 | 2 | 0 | 0 | + | + | + | + | + | + | + | + | + | 0 |
| 15313 | 1 | 0 | 0 | + | + | + | + | + | + | + | + | + | 0 |
| 15313 | 2 | 0 | 0 | + | + | + | + | + | + | + | + | + | 0 |
| 19418 | 1 | 0 | 0 | 0 | 0 | + | + | + | + | + | + | + | 0 |
| 19418 | 2 | 0 | 0 | 0 | 0 | + | + | + | + | + | + | + | 0 |
| 33560[c] | 1 | 0 | 0 | + | 0 | + | + | + | + | + | + | + | 0 |
| 33560[c] | 2 | 0 | 0 | + | 0 | + | + | + | + | + | + | + | 0 |
| 33592 | 1 | 0 | 0 | + | + | + | + | + | + | + | + | + | 0 |
| 33592 | 2 | 0 | 0 | + | + | + | + | + | + | + | + | + | 0 |
| 43895 | 1 | 0 | 0 | + | 0 | + | + | + | + | + | + | + | 0 |
| 43895 | 2 | 0 | 0 | 0 | + | + | + | + | + | + | + | + | 0 |
| 51559 | 1 | 0 | + | + | + | + | + | + | + | + | + | + | 0 |
| 51559 | 2 | 0 | + | + | + | + | + | + | + | + | + | + | 0 |

[a] Incubation temperature $25 \pm 2°$ C. rather than $37 \pm 2°$ C.
[b] Incubation temperature $30 \pm 2°$ C. rather than $37 \pm 2°$ C.
[c] Incubation time of about 25.50 hours at incubation temperature of $42 \pm 2°$ C. with a 5% $CO_2$ atmosphere Rapid Germicidal Studies The rapid germicidal studies are used to measure the ability of an antibacterial agent to rapidly reduce a known population of microorganisms. An aliquot of the antibacterial test material is contacted with a known concentration of test bacteria or fungi for a predetermined period of time. The test material is then neutralized, the concentration of the surviving microorganisms is determined, and the efficacy of the antibacterial agent is calculated based on the percentage of microorganisms that did not survive exposure to the antibacterial agent. or example, the product of Example 2 ("Product 2") is evaluated for rapid germicidal activity using a protocol wherein a 5 mL aliquot of undiluted Product 2 is placed in a sterile glass jar at $25 \pm 1°$ C. and a 0.5 mL sample of a selected microorganism broth culture yielding an approximate microorganism dilution of about $10^8$ CFU/mL is mixed into the antibacterial material aliquot. After waiting a prescribed time ("exposure time"), 45 mL of a neutralizer solution is added to the glass jar and stirred for 60 seconds. A 1 mL aliquot is removed from the jar—having a microorganism dilution of about $10^{-1}$—and 10-fold serial dilutions are made to reach a dilution of about $10^{-6}$. The dilutions are plated in duplicate using a Pour Plate Technique. The plates are inverted and incubated at 35±2° C. for 48±2 hours. Following incubation, the colony forming units per mL (CFU/mL) for surviving organisms are counted and compared to the starting populations. Control samples are included for each organism and exposure time following essentially the same procedure except that the Product 2 is not added in the initial step of the procedure. Table 4 lists microorganisms for use in the Rapid Germicidal Study, the number of colony forming units per mL for the controls and the test samples (reported in replicate), and the efficacy of the Product 2 as determined by percent reduction in organism count and the $\log_{10}$ reduction.

TABLE 4

| Organism ATCC # | Exposure Time (sec) | Count for Control (CFU/mL) | Count for Test Sample | | % Reduction | $\log_{10}$ Reduction |
|---|---|---|---|---|---|---|
| | | | Rep 1 (CFU/mL) | Rep 2 (CFU/mL) | | |
| 06275 | 15 | $2.0 \times 10^7$ | $3.2 \times 10^3$ | $3.4 \times 10^3$ | 99.98 | 3.78 |
| 06275 | 30 | $1.7 \times 10^7$ | $1.4 \times 10^3$ | $2.3 \times 10^4$ | 99.93 | 3.15 |
| 06275 | 60 | $1.4 \times 10^7$ | $1.8 \times 10^4$ | $5.5 \times 10^3$ | 99.91 | 3.07 |
| 06303 | 15 | $9.7 \times 10^6$ | $6.0 \times 10^1$ | $3.3 \times 10^3$ | 99.98 | 3.76 |
| 06303 | 30 | $1.4 \times 10^7$ | $6.1 \times 10^2$ | $1.1 \times 10^2$ | >99.99 | >4.59 |
| 06303 | 60 | $9.9 \times 10^6$ | $<1.0 \times 10^1$ | $<1.0 \times 10^1$ | >99.99 | >6.00 |
| 06538 | 15 | $3.4 \times 10^7$ | $<1.0 \times 10^1$ | $<1.0 \times 10^1$ | >99.99 | >6.53 |
| 06538 | 30 | $3.1 \times 10^7$ | $<1.0 \times 10^1$ | $<1.0 \times 10^1$ | >99.99 | >6.49 |
| 06538 | 60 | $3.4 \times 10^7$ | $<1.0 \times 10^1$ | $<1.0 \times 10^1$ | >99.99 | >6.53 |
| 06538 | 15 | $6.0 \times 10^7$ | $5.0 \times 10^4$ | $8.4 \times 10^3$ | 99.95 | 3.23 |
| 06538 | 30 | $3.7 \times 10^7$ | $1.6 \times 10^4$ | $<1.0 \times 10^1$ | >99.98 | >3.67 |
| 06538 | 60 | $4.6 \times 10^7$ | $1.2 \times 10^2$ | $5.0 \times 10^1$ | >99.99 | 5.73 |
| 06539 | 15 | $1.9 \times 10^7$ | $<1.0 \times 10^1$ | $<1.0 \times 10^1$ | >99.99 | >6.28 |
| 06539 | 30 | $1.6 \times 10^7$ | $6.0 \times 10^3$ | $<1.0 \times 10^1$ | >99.98 | >3.72 |
| 06539 | 60 | $2.3 \times 10^7$ | $3.5 \times 10^3$ | $2.7 \times 10^2$ | 99.99 | 4.08 |
| 07002 | 15 | $2.0 \times 10^7$ | $<1.0 \times 10^1$ | $1.4 \times 10^3$ | >99.99 | >4.46 |
| 07002 | 30 | $2.6 \times 10^7$ | $1.1 \times 10^4$ | $<1.0 \times 10^1$ | >99.98 | >3.67 |
| 07002 | 60 | $2.3 \times 10^7$ | $<1.0 \times 10^1$ | $<1.0 \times 10^1$ | >99.99 | >6.36 |
| 09027 | 15 | $2.0 \times 10^7$ | $2.9 \times 10^2$ | $<1.0 \times 10^1$ | >99.99 | >5.12 |
| 09027 | 30 | $1.4 \times 10^8$ | $2.4 \times 10^5$ | $<1.0 \times 10^1$ | 99.91 | 3.07 |
| 09027 | 60 | $1.3 \times 10^8$ | $<1.0 \times 10^1$ | $2.8 \times 10^4$ | >99.99 | >3.96 |
| 09027 | 15 | $1.3 \times 10^8$ | $7.0 \times 10^4$ | $2.3 \times 10^4$ | 99.97 | 3.45 |
| 09027 | 30 | $2.0 \times 10^7$ | $<1.0 \times 10^1$ | $<1.0 \times 10^1$ | >99.99 | >6.30 |
| 09027 | 60 | $2.8 \times 10^7$ | $<1.0 \times 10^1$ | $1.0 \times 10^1$ | >99.99 | >6.45 |
| 10231 | 15 | $1.0 \times 10^6$ | $1.5 \times 10^4$ | $1.4 \times 10^3$ | 99.18 | 2.09 |
| 10231 | 30 | $1.0 \times 10^6$ | $8.6 \times 10^2$ | $1.5 \times 10^1$ | 99.96 | 3.36 |
| 10231 | 60 | $9.8 \times 10^5$ | $1.2 \times 10^2$ | $3.4 \times 10^3$ | 99.82 | 2.73 |
| 10231 | 15 | $1.1 \times 10^6$ | $7.5 \times 10^1$ | $1.3 \times 10^3$ | 99.94 | 3.20 |
| 10231 | 30 | $9.8 \times 10^5$ | $1.8 \times 10^4$ | $<1.0 \times 10^1$ | >99.08 | >2.04 |
| 10231 | 60 | $8.8 \times 10^5$ | $2.8 \times 10^2$ | $1.2 \times 10^2$ | 99.98 | 3.64 |
| 11229 | 15 | $4.0 \times 10^7$ | $<1.0 \times 10^1$ | $<1.0 \times 10^1$ | >99.99 | >6.60 |
| 11229 | 30 | $2.8 \times 10^7$ | $<1.0 \times 10^1$ | $<1.0 \times 10^1$ | >99.99 | >6.45 |
| 11229 | 60 | $3.6 \times 10^7$ | $<1.0 \times 10^1$ | $<1.0 \times 10^1$ | >99.99 | >6.56 |
| 11296 | 15 | $2.4 \times 10^7$ | $2.0 \times 10^3$ | $1.6 \times 10^3$ | 99.99 | 4.12 |
| 11296 | 30 | $2.0 \times 10^7$ | $1.1 \times 10^3$ | $6.5 \times 10^1$ | 99.99 | 4.54 |
| 11296 | 60 | $2.1 \times 10^7$ | $3.8 \times 10^3$ | $<1.0 \times 10^1$ | >99.99 | >4.04 |
| 11778 | 15 | $8.2 \times 10^5$ | $1.8 \times 10^3$ | $<1.0 \times 10^1$ | >99.89 | >2.96 |
| 11778 | 30 | $8.2 \times 10^5$ | $<1.0 \times 10^1$ | $<1.0 \times 10^1$ | >99.99 | >4.91 |
| 11778 | 60 | $8.6 \times 10^5$ | $2.6 \times 10^3$ | $1.0 \times 10^1$ | 99.85 | 2.82 |
| 12228 | 15 | $1.4 \times 10^7$ | $9.6 \times 10^3$ | $8.4 \times 10^4$ | 99.66 | 2.48 |
| 12228 | 30 | $1.2 \times 10^7$ | $1.5 \times 10^3$ | $5.0 \times 10^4$ | 99.78 | 2.66 |
| 12228 | 60 | $1.4 \times 10^7$ | $1.5 \times 10^1$ | $7.2 \times 10^3$ | 99.97 | 3.59 |
| 15313 | 15 | $4.3 \times 10^7$ | $3.0 \times 10^5$ | $1.8 \times 10^5$ | 99.44 | 2.25 |
| 15313 | 30 | $4.7 \times 10^7$ | $<1.0 \times 10^1$ | $6.9 \times 10^3$ | >99.99 | >4.14 |
| 15313 | 60 | $4.8 \times 10^7$ | $3.4 \times 10^4$ | $1.7 \times 10^5$ | 99.79 | 2.68 |
| 19418 | 15 | $1.7 \times 10^7$ | $3.5 \times 10^2$ | $4.7 \times 10^3$ | 99.99 | 3.85 |
| 19418 | 30 | $1.5 \times 10^7$ | $1.2 \times 10^4$ | $5.0 \times 10^4$ | 99.79 | 2.69 |
| 19418 | 60 | $1.6 \times 10^7$ | $1.0 \times 10^3$ | $9.8 \times 10^3$ | 99.97 | 3.47 |
| 22019 | 15 | $9.0 \times 10^5$ | $1.0 \times 10^3$ | $6.0 \times 10^3$ | 99.61 | 2.41 |
| 22019 | 30 | $9.5 \times 10^5$ | $6.2 \times 10^2$ | $5.4 \times 10^2$ | 99.94 | 3.22 |
| 22019 | 60 | $1.6 \times 10^6$ | $<1.0 \times 10^1$ | $<1.0 \times 10^1$ | >99.99 | >5.20 |
| 33592 | 15 | $1.4 \times 10^7$ | $7.4 \times 10^4$ | $2.6 \times 10^5$ | 98.78 | 1.92 |
| 33592 | 30 | $1.1 \times 10^7$ | $<1.0 \times 10^1$ | $2.2 \times 10^3$ | >99.99 | >4.00 |
| 33592 | 60 | $1.4 \times 10^7$ | $1.6 \times 10^3$ | $1.8 \times 10^3$ | 99.99 | 3.92 |
| 33650 | 15 | $5.6 \times 10^6$ | $6.0 \times 10^2$ | $1.8 \times 10^3$ | 99.98 | 3.67 |
| 33650 | 30 | $4.9 \times 10^6$ | $<1.0 \times 10^1$ | $<1.0 \times 10^1$ | >99.99 | >5.69 |
| 33650 | 60 | $6.2 \times 10^6$ | $3.0 \times 10^1$ | $<1.0 \times 10^1$ | >99.99 | >5.19 |
| 43895 | 15 | $4.2 \times 10^7$ | $<1.0 \times 10^1$ | $<1.0 \times 10^1$ | >99.99 | >6.62 |
| 43895 | 30 | $4.8 \times 10^7$ | $5.3 \times 10^3$ | $<1.0 \times 10^1$ | >99.99 | >4.27 |
| 43895 | 60 | $3.0 \times 10^7$ | $<1.0 \times 10^1$ | $<1.0 \times 10^1$ | >99.99 | >6.48 |

TABLE 4-continued

| Organism ATCC # | Exposure Time (sec) | Count for Control (CFU/mL) | Count for Test Sample Rep 1 (CFU/mL) | Count for Test Sample Rep 2 (CFU/mL) | % Reduction | Log$_{10}$ Reduction |
|---|---|---|---|---|---|---|
| 51559 | 15 | $4.0 \times 10^7$ | $4.0 \times 10^1$ | $<1.0 \times 10^1$ | >99.99 | >6.02 |
| 51559 | 30 | $4.6 \times 10^7$ | $<1.0 \times 10^1$ | $<1.0 \times 10^1$ | >99.99 | >6.66 |
| 51559 | 60 | $8.8 \times 10^5$ | $4.0 \times 10^3$ | $<1.0 \times 10^1$ | >99.99 | >4.30 |

From a reading of the above, one with ordinary skill in the art should be able to devise variations to the inventive features. For example, other additives may be included in the formulation to increase consumer acceptance, such as dyes, colorants, skin-softening agents, skin-protecting agents, such as sunscreening materials, and other silicone or non-silicone compounds or solvents that may modify the drying characteristics of alcohols or change the tactile feel and dryness caused by high alcohol containing systems. These and other variations are believed to fall within the spirit and scope of the attached claims.

What is claimed is:

1. A waterless sanitizing hand cleanser consistently essentially of:
   from about 60 wt. % to about 90 wt. % of one or more organic alcohols;
   from about 5 wt. % to about 35 wt. % of one or more silicone based materials;
   up to about 5 wt. % of one or more humectants;
   up to about 12 wt. % of one or more skin pH-maintaining additive; and
   one or more thickening agents added at a concentration so as to produce a product with a viscosity in the range of 100 cp to 100,000 cp at about 25° C.

2. The hand cleanser of claim 1 wherein said alcohol is selected from anhydrous ethanol, isopropyl alcohol, propanol, butanol, phenylethyl alcohol, benzyl alcohol and a combination thereof.

3. The hand cleanser of claim 1 wherein said pH-maintaining additives allow the skin to maintain a pH of from about 4.0 to about 6.0.

4. The hand cleanser of claim 3 wherein said pH-maintaining additives are selected from the group consisting of fumed silica, lactic acid, sodium lactate or a combination thereof.

5. The hand cleanser of claim 3 wherein said pH-maintaining additive is fumed silica.

6. The hand cleanser of claim 5 wherein said fumed silica is added at a concentration up to about 5.0 wt. %.

7. The hand cleanser of claim 3 wherein said pH-maintaining additive is lactic acid.

8. The hand cleanser of claim 7 wherein said lactic acid is added at a concentration up to about 5.0 wt. %.

9. The hand cleanser of claim 6 further including lactic acid added at a concentration up to about 5.0 wt. %.

10. The hand cleanser of claim 3 wherein said pH-maintaining additive is sodium lactate.

11. The hand cleanser of claim 10 wherein said sodium lactate is added at a concentration up to about 2.0 wt. %.

12. The hand cleanser of claim 1 wherein said silicone based material is cyclomethicone, trimethylsiloxysilicate or a combination thereof.

13. The hand cleanser of claim 1 wherein said humectant is isopropyl myristate.

14. The hand cleanser of claim 1 wherein said thickening agent is a cellulose based thickener.

15. The hand cleanser of claim 14 wherein said thickening agent is methyl cellulose.

16. The hand cleanser of claim 1 wherein said thickening agent is fumed silica.

17. The hand cleanser of claim 16 wherein said fumed silica is present at concentrations up to about 5 wt. %.

18. The hand cleanser of claim 1 further including a fragrance.

19. The hand cleanser of claim 18 wherein said fragrance is added at a concentration up to about 1.5 wt. %.

20. The hand cleanser of claim 1 further including a colorant.

21. The hand cleanser of claim 1 further including one or more emollients.

22. The hand cleanser of claim 21 wherein said emollients are added at a concentration up to about 5 wt. %.

23. The hand cleanser of claim 22 wherein said emollients are selected from the group consisting of tea tree oil, hemp oil, aloe-based oil or a combination thereof.

24. The hand cleanser of claim 1 wherein said viscosity is in the range of from about 250 cp to about 450 cp at about 25° C.

25. A sanitizing hand cleanser consisting essentially of:
   a) an alcohol mixture, prepared by mixing from about 60 wt. % to about 90 wt. % of one or more alcohols with from about 5 wt. % to about 35 wt. % of one or more silicone based materials, up to about 5 wt. % isopropyl myristate, up to about 5.0 wt. % lactic acid and up to about 2.0 wt. % sodium lactate at ambient temperature until well blended; and
   b) a thickening mixture, prepared by removing a portion of said alcohol mixture to a separate mixing vessel and adding up to about 1.5 wt. % methyl cellulose while maintaining continuous mixing,
      wherein said thickening mixture is combined with said alcohol mixture at ambient temperature and with continuous mixing until reaching a product viscosity of from about 250 cp to about 450 cp at about 25° C., said alcohol mixture and said thickening mixture being prepared in the absence of water.

26. The hand cleanser of claim 25 wherein said alcohol is selected from anhydrous ethanol, isopropyl alcohol, propanol, butanol, phenylethyl alcohol, benzyl alcohol and a combination thereof.

27. The hand cleanser of claim 25 wherein said silicone based material is cyclomethicone, trimethylsiloxysilicate and a combination thereof.

28. The hand cleanser of claim 25 further including from up to about 5 wt. % fumed silica added to said thickening mixture.

29. The hand cleanser of claim 25 further including a fragrance added at a concentration up to about 1.5 wt. % to said alcohol mixture.

30. The hand cleanser of claim 25 further including up to about 5 wt. % of one or more emollients selected from the group consisting of tea tree oil, hemp oil, aloe-based oil or a combination thereof, said emollients being added to said alcohol mixture.

31. A method of making a sanitizing hand cleanser consistently essentially of the steps of:
   a) mixing from about 60 wt. % to about 90 wt. % of one or more alcohols with from about 5 wt. % to about 35 wt. % of one or more silicone based materials, up to about 5 wt. % isopropyl myristate, up to about 5.0 wt. % lactic acid and up to about 2.0 wt. % sodium lactate at ambient temperature until well blended;
   b) adding up to about 1.5 wt. % methyl cellulose to a portion of said mixture formed in step a) and mixing until well blended; and
   c) adding said methyl cellulose mixture to said mixture formed in step a) at ambient temperature and with continuous mixing until reaching a product viscosity of from about 250 cp to about 450 cp at about 25° C.

32. The hand cleanser of claim 31 wherein said organic alcohol is selected from anhydrous ethanol, isopropyl alcohol, propanol, butanol, phenylethyl alcohol, benzyl alcohol and a combination thereof.

33. The hand cleanser of claim 31 wherein said silicone based material is cyclomethicone, trimethylsiloxysilicate or a combination thereof.

34. The hand cleanser of claim 31 further including up to about 5 wt. % fumed silica added to said thickening mixture.

35. The hand cleanser of claim 31 further including a fragrance added at a concentration up to about 1.5 wt. % to said alcohol mixture.

36. The hand cleanser of claim 31 further including up to about 5 wt. % of one or more emollients selected from the group consisting of tea tree oil, hemp oil, aloe-based oil or a combination thereof, said emollients being added to said alcohol mixture.

37. A waterless sanitizing hand cleanser comprising:
   from about 60 wt. to about 90 wt. % of one or more alcohols;
   from about 11 wt. % to about 35 wt. % of one or more silicone based materials;
   up to about 5 wt. % of one or more humectants;
   up to about 10 wt. % of one or more antimicrobial agents;
   up to about 12 wt. % of one or more skin pH-maintaining additive; and
   one or more thickening agents added at a concentration so as to produce a product with a viscosity in the range of 100 cp to 100,000 cp at about 25° C.

38. The hand cleanser of claim 37 wherein said alcohol is selected from anhydrous ethanol, isopropyl alcohol, propanol, butanol, phenylethyl alcohol, benzyl alcohol and a combination thereof.

39. The hand cleanser of claim 37 wherein said pH-maintaining additives allow the skin to maintain a pH of from about 4.0 to about 6.0.

40. The hand cleanser of claim 39 wherein said pH-maintaining additives are selected from the group consisting of fumed silica, lactic acid, sodium lactate and combination thereof.

41. The hand cleanser of claim 40 wherein said pH-maintaining additive is fumed silica added at a concentration up to about 5 wt. %.

42. The hand cleanser of claim 40 wherein said pH-maintaining additive is lactic acid added a concentration up to about 5.0 wt. %.

43. The hand cleanser of claim 41 further including lactic acid added at a concentration up to about 5.0 wt. %.

44. The hand cleanser of claim 40 wherein said pH-maintaining additive is sodium lactate is added at a concentration up to about 2.0 wt. %.

45. The hand cleanser of claim 37 wherein said silicone based material is cyclomethicone, trimethylsiloxysilicate and a combination thereof.

46. The hand cleanser of claim 37 wherein said humectant is isopropyl myristate.

47. The hand cleanser of claim 37 wherein said thickening agent is a cellulose based thickener.

48. The hand cleanser of claim 47 wherein said thickening agent is methyl cellulose.

49. The hand cleanser of claim 37 wherein said thickening agent is fumed silica present at concentrations up to about 0 wt. % to about 5 wt. %.

50. The hand cleanser of claim 1 further including a fragrance added at a concentration up to about 1.5 wt. %.

51. The hand cleanser of claim 1 further including one or more emollients are added at a concentration up to about 5 wt. %.

52. The hand cleanser of claim 51 wherein said emollients are selected from the group consisting of tea tree oil, hemp oil, aloe-based oil and a combination thereof.

53. The hand cleanser of claim 37 wherein said viscosity is in the range of from about 250 cp to about 450 cp at about 25° C.

54. The hand cleanser of claim 37 wherein said antimicrobial agents are selected from the group consisting of para-chloro-meta-xylenol, chlorhexidine gluconate, triclosan, quaternary ammonium salts and combinations thereof.

55. The hand cleanser of claim 37 wherein said antimicrobial agent is para-chloro-meta-xylenol added at a concentration of from about 2 wt. % to about 3.75 wt. %.

56. The hand cleanser of claim 37 wherein said alcohol is present at a concentration of from about 74 wt. % to about 77 wt. %, said silicone based material is present at a concentration of from about 14 wt. % to about 17 wt. % and said antimicrobial agent is present at a concentration of from about 1 wt % to about 3.75 wt. %.

57. The hand cleanser of claim 1 further comprising incorporating the product into a surgical scrub brush.

58. The hand cleanser of claim 37 further comprising incorporating the product into a surgical scrub brush.

59. The hand cleanser of claim 37 further comprising incorporating the product into a wipe.

60. The hand cleanser of claim 37 further comprising incorporating the product into a wipe.

* * * * *